US012721664B2

(12) United States Patent
Barrus

(10) Patent No.: US 12,721,664 B2
(45) Date of Patent: Sep. 1, 2026

(54) SET SCREW RETAINING DRIVER

(71) Applicant: K2M, Inc., Leesburg, VA (US)

(72) Inventor: Michael Barrus, Redondo Beach, CA (US)

(73) Assignee: Stryker Corporation, Portage, MI (US)

( * ) Notice: Subject to any disclaimer, the term of this patent is extended or adjusted under 35 U.S.C. 154(b) by 261 days.

(21) Appl. No.: 18/566,266

(22) PCT Filed: Jun. 3, 2022

(86) PCT No.: PCT/US2022/032072
§ 371 (c)(1),
(2) Date: Dec. 1, 2023

(87) PCT Pub. No.: WO2022/256599
PCT Pub. Date: Dec. 8, 2022

(65) Prior Publication Data

US 2024/0245441 A1 Jul. 25, 2024

Related U.S. Application Data

(60) Provisional application No. 63/196,747, filed on Jun. 4, 2021.

(51) Int. Cl.
*A61B 17/70* (2006.01)
*A61B 17/88* (2006.01)
*A61B 17/00* (2006.01)

(52) U.S. Cl.
CPC ...... *A61B 17/8888* (2013.01); *A61B 17/7091* (2013.01); *A61B 17/888* (2013.01); *A61B 2017/00367* (2013.01)

(58) Field of Classification Search
CPC ... B25B 23/105; B25B 23/106; B25B 23/108; A61B 17/8888
See application file for complete search history.

(56) References Cited

U.S. PATENT DOCUMENTS 192,423 A 6/1877 Elterich
3,288,184 A 11/1966 Kyser
(Continued)

FOREIGN PATENT DOCUMENTS

WO 2019/102249 A1 5/2019

OTHER PUBLICATIONS

International Search Report and Written Opinion issued in Appln. No. PCT/US2022/032072 mailed Nov. 17, 2022 (20 pages).

*Primary Examiner* — Nicholas W Woodall
(74) *Attorney, Agent, or Firm* — Lerner David LLP

(57) ABSTRACT

A tool (100) for use with a fastener includes a drive shaft (110) extending along a longitudinal axis (X) from a proximal end (102) to a distal end (104). The tool has an engaging tip (122) at the distal end (104) of the drive shaft (110) sized and shaped to detachably engage a fastener such that the engaging tip (122) is rotationally fixed to the fastener when the engaging tip (122) is engaged with the fastener. The tool (100) further includes a compressible engagement member (150) detachably coupled to the drive shaft (110). The compressible engagement member (150) extends from the engaging tip (122) and is sized and shaped to detachably engage with a receiving portion of the fastener. In an undeformed configuration, the compressible engagement member (150) has a width greater than the receiving portion.

9 Claims, 9 Drawing Sheets

(56) References Cited

U.S. PATENT DOCUMENTS

| | | | | |
|---|---|---|---|---|
| 4,553,455 | A | 11/1985 | Wilcox et al. | |
| 5,534,001 | A | 7/1996 | Schlapfer et al. | |
| 6,206,696 | B1 | 3/2001 | Day | |
| 6,648,888 | B1 | 11/2003 | Shluzas | |
| 7,452,361 | B2 * | 11/2008 | Kreidler | B25B 23/106 606/305 |
| 8,500,748 | B2 * | 8/2013 | Yu | A61B 17/888 606/99 |
| 10,874,448 | B2 | 12/2020 | Rees et al. | |
| 11,540,867 | B2 * | 1/2023 | Perrow | A61B 17/8888 |
| 12,515,301 | B2 * | 1/2026 | Lang | B25B 23/105 |
| 2002/0198534 | A1 * | 12/2002 | White | A61B 17/8888 606/104 |
| 2005/0033307 | A1 | 2/2005 | Cook et al. | |
| 2008/0269768 | A1 | 10/2008 | Schwager et al. | |
| 2011/0132154 | A1 * | 6/2011 | Huang | B25B 23/108 81/444 |
| 2012/0123431 | A1 * | 5/2012 | Robinson | A61B 17/808 606/104 |
| 2017/0181776 | A1 | 6/2017 | Beretta et al. | |
| 2017/0303981 | A1 * | 10/2017 | Myers | A61B 17/8888 |
| 2017/0305000 | A1 * | 10/2017 | Kennedy | B25B 23/106 |
| 2018/0368902 | A1 | 12/2018 | Milor et al. | |
| 2020/0269398 | A1 * | 8/2020 | Donovan | F16B 23/003 |

* cited by examiner

390

300

380

SET SCREW RETAINING DRIVER

CROSS-REFERENCE TO RELATED APPLICATIONS

The present application is a national phase entry under 35 U.S.C. § 371 of International Application No. PCT/US2022/032072, filed Jun. 3, 2022, published in English, which claims the benefit of U.S. Provisional Patent Application Ser. No. 63/196,747, filed Jun. 4, 2021, the disclosures of which are incorporated herein by reference.

BACKGROUND OF THE INVENTION

Fastener-driving tools come in various shapes and sizes for mating with fasteners. A firm, stable grip is strongly desired between the tool and the fastener so that the tool can be rotatably fixed to the receiving portion of the fastener (e.g., a screwhead) to smoothly actuate the fastener. Anything less than a strong engagement may result in the inability to provide enough torque to fully actuate the fastener and any relative rotation between the tool and the fastener (e.g., slippage) may lead to deformation of the fastener and eventually an inability to actuate the fastener. As such, different shapes and structures have been developed to improve the engagement between such tools and fasteners.

In the context of surgical procedures, another problem that often arises is the inability to hold the fastener in engagement with the tool. Such procedures are often performed in limited spaces that don't permit for the holding of the fastener in engagement with the tool, as would be done in, for instance, a carpentry setting. Indeed, it is often beneficial to provide a driver that includes structure to self-retain the fastener thereto.

One such structure for a driving tool is a bifurcated tip at the distal end of the tool, which defines a gap between the split tip when the tool is at rest. The split tip may be compressed inwardly when inserted into the screwhead such that the split tip applies an outward biasing force against the screwhead and creates a sturdy engagement between the tool and the screw. However, the compressible and more fragile nature of the split tip makes such a structure more susceptible to breaking. Further, driving tools used in surgical environments may demand higher maintenance of cleanliness and sterility, which may be difficult or inefficient with monolithically formed tools.

Thus, further developments in the art of bifurcated tip driving tools are therefore desired.

BRIEF SUMMARY OF THE INVENTION

The present disclosure describes a modular tool that can be used to engage and actuate a fastener. In some examples, the tool is a set screw retaining driver that is configured to securely engage and actuate a set screw during the implantation of a spinal rod in a patient. The tool includes an engaging tip shaped to engage a receiving portion of a set screw to rotationally fix the tool to the set screw, allowing an operator to rotate the tool to cause rotation of the set screw. The tool further includes an element having a bifurcated tip which is adapted to be compressed within the receiving portion of the set screw and spring outwardly to further secure the engagement between the tool and the set screw. The bifurcated element is detachably coupled to the shaft of the tool such that the bifurcated element may be conveniently removed or replaced with ease.

In one aspect of the disclosure, a tool for use with a fastener may include a drive shaft extending along a longitudinal axis from a proximal end to a distal end, an engaging tip at the distal end, the engaging tip sized and shaped to detachably engage a fastener, wherein the engaging tip is rotationally fixed to the fastener when the engaging tip is engaged with the fastener, and a compressible engagement member detachably coupled to the drive shaft, the compressible engagement member extending from the engaging tip sized and shaped to detachably engage with a receiving portion of the fastener. In an undeformed configuration, the compressible engagement member may have a width greater than the receiving portion. In a compressed configuration, the compressible engagement member may have a width less than the receiving portion. The drive shaft may have a distal portion adjacent the engaging tip, and the engaging tip and the distal portion may define a cavity extending along the longitudinal axis.

The compressible engagement member may extend along the longitudinal axis from a proximal end to a distal end, and the compressible engagement member may include a stem extending from the proximal end. The compressible engagement member may include a first branch and a second branch extending distally from the stem. The compressible engagement member may include a first head portion coupled to a distal end of the first branch and a second head portion coupled to a distal end of the second branch. When the compressible engagement member is in the undeformed configuration, the first and second branches may define a gap therebetween and the first and second head portions may define a gap therebetween in communication with the gap between the branches. The first and second head portions may have a tapered distal surface sized and positioned to contact the fastener when the tool is being engaged with the fastener, such that the fastener applies a compressive force to the head portions to transition the compressible engagement member from an undeformed configuration to a compressed configuration.

The stem may extend into the cavity of the distal portion of the drive shaft in an assembled configuration. A proximal portion of the stem may define an aperture therethrough for receiving a fixation device. The drive shaft may define a first aperture configured to receive the fixation device. The drive shaft may define a second aperture opposite and aligned with the first aperture sized, shaped and positioned to receive the fixation device. In an assembled configuration, the aperture of the stem may be aligned with the first and second apertures of the drive shaft to receive a single fixation device through each of the apertures. The fixation device may be configured to be removed from the apertures of the drive shaft and the compressible engagement member to decouple the compressible engagement member from the drive shaft. The engaging tip may be corrugated around a circumference of the engaging tip, defining a plurality of ridges and a rounded groove between each adjacent pair of ridges. The engaging tip may include a plurality of fingers extending from the drive shaft, each adjacent pair of fingers defining a gap therebetween.

According to another aspect of the disclosure, a method of using a tool for use with a fastener may include inserting an engaging tip and a first head portion and a second head portion of a compressible engagement member defining a gap therebetween into a receiving portion of the fastener; applying pressure between distal tapered surfaces of the first and second head portions and the receiving portion of the fastener to compress the first head portion and the second portion head toward each other within the receiving portion;

and rotating the tool to rotate the fastener. The method may further include removing the compressible engagement member and the engaging tip of the tool from the fastener; and decoupling the compressible engagement member from a drive shaft of the tool. Decoupling the compressible engagement member from the drive shaft may include removing a fixation device extending through at least one aperture of the drive shaft and an aperture of the compressible engagement member. Decoupling the compressible engagement member from the drive shaft may include pulling the compressible engagement member distally relative to the drive shaft to remove the compressible engagement member from a distal cavity of the drive shaft. The method may further include after decoupling the compressible engagement member from the drive shaft, coupling a second compressible engagement member to the drive shaft. Coupling the second compressible engagement member to the drive shaft may include inserting a proximal end of the second compressible engagement member into a distal cavity of the drive shaft. Coupling the second compressible engagement member to the drive shaft may include aligning an aperture of the compressible engagement member with an aperture of the drive shaft and inserting a fixation device through the apertures.

According to another aspect of the disclosure, a kit for a tool for use with a fastener may include a drive shaft extending from a proximal end to a distal end along a longitudinal axis, the drive shaft having an engaging tip for engaging with the fastener and a cavity at the distal end, and a compressible engagement member adapted to be inserted into the distal cavity of the drive shaft to be coupled to the drive shaft. The kit may further include a plurality of compressible engagement members adapted for disposable use with the drive shaft. The fastener may have a receiving portion to correspondingly mate with the engaging tip of the drive shaft and a distal end of the compressible engagement member.

DETAILED DESCRIPTION

As used herein, the term "proximal." when used in connection with a device, or components of a device, refers to the end of the device closer to the user when the device is being used as intended. On the other hand, the term "distal," when used in connection with a device, components of a device, refers to the end of the device or implant farther away from the user when the device is being used as intended. As used herein, the terms "about," "generally," "approximately," and "substantially" are intended to mean that slight deviations from absolute are included within the scope of the term so modified.

The device described in the present disclosure is referred to and may be used as a set screw retaining driver. However, it should be understood that the disclosed device is not limited to use with set screws, but may be used for forming a detachable engagement with any object in a rotatably fixed manner, typically for the purpose of actuating (e.g., rotating) the object. For example, the tool may be used with any fastener, such as a bone, wood or metal screw.

Figure 1:
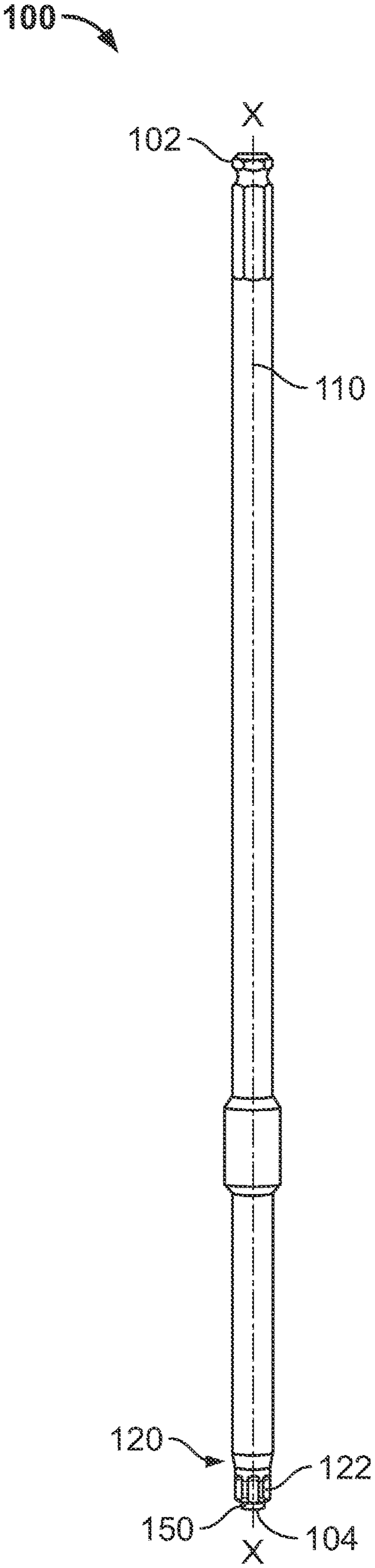
FIG. 1 is a front view of a retaining driver according to an embodiment of the disclosure.

FIG. 1 illustrates a retaining driver 100 according to an embodiment of the disclosure. Retaining driver 100 is elongate, extending from a proximal end 102 to a distal end 104 along a longitudinal axis X. Proximal end 102 and portions of the driver near the proximal end 102 are intended to be grasped and wielded by an operator, such as a surgeon. Such portions may also be engageable with a secondary tool, such as a powered handpiece or the like.

Figure 2:
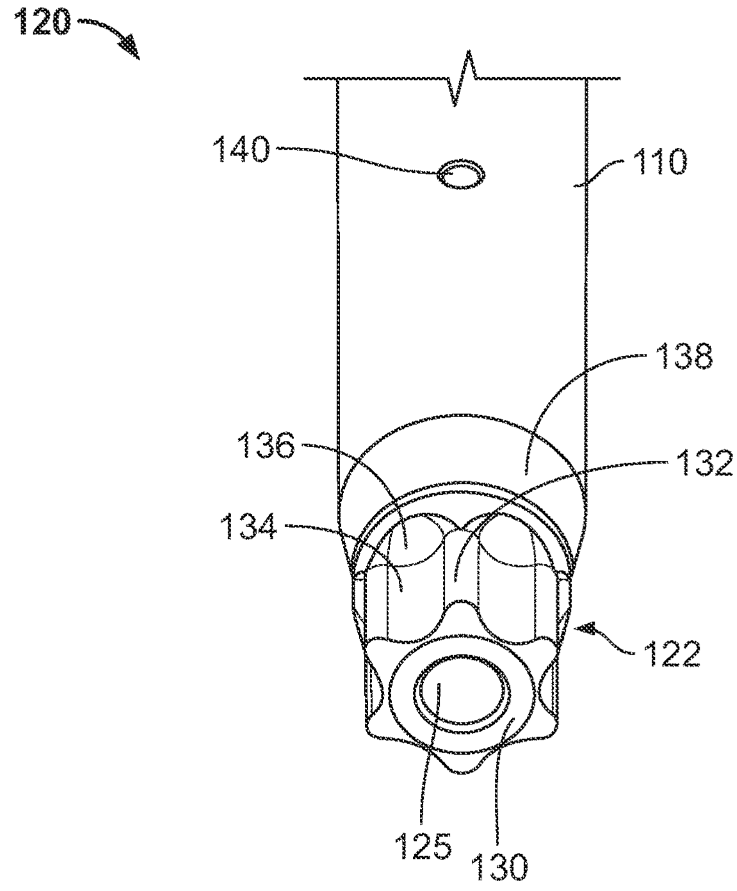
FIGS. 2-3 are perspective and distal views, respectively, of a distal portion of a drive shaft and a distal tip of the retaining driver of FIG. 1.
Figure 3:
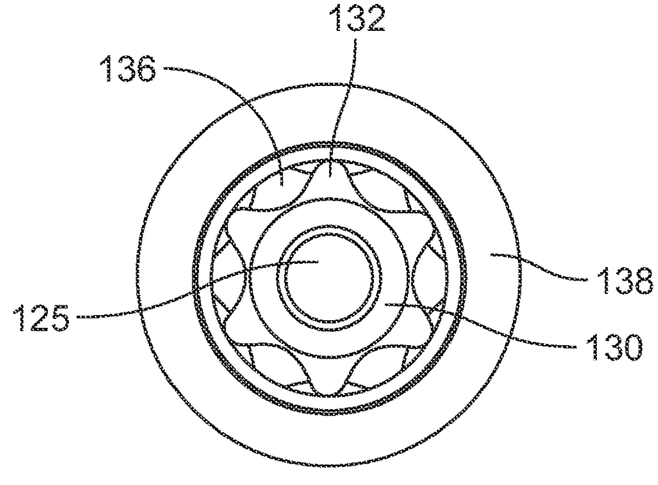

Retaining driver 100 includes a drive shaft 110 extending along axis X and an engaging tip 122 extending distally from the drive shaft 110 sized and shaped to mate with a set screw, and a compressible engagement member 150 coupled to the drive shaft 110. A close-up view of a distal portion 120 of retaining driver 100 and engaging tip 122 is shown in FIGS. 2-3. It should be noted that FIGS. 2-3 illustrate driver 100 without compressible engagement member 150 (described further below) for ease of illustration. Drive shaft 110 includes a tapered portion 138 at its distal end that tapers radially inward as it extends distally. Engaging tip 122 extends distally from tapered portion 138, having a circular base 130 and a generally corrugated circumference surrounding the circular base 130. That is, engaging tip 122 includes a plurality of ridges 132 spaced evenly apart along the circumference of engaging tip 122, each ridge 132 protruding radially from the circular base 130 and extending in a direction parallel to longitudinal axis X. Each pair of adjacent ridges 132 is separated by an elongate rounded groove 134, and each elongate rounded groove 134 has a proximal rounded groove 136 in communication with and located proximally relative to the elongate rounded groove 134. Circular base 130 is hollow and defines a cavity 125 which extends through engaging tip 122 and distal portion 120 of driver 100 along longitudinal axis X. The cavity 125 is also in communication with an aperture 140 located on distal portion 120 of drive shaft 110.

As noted above, engaging tip 122 is sized and shaped to mate with a set screw having a corresponding female mating portion that is sized and shaped for receiving the engaging tip 122 of the retaining driver 100. It is contemplated that drive shaft 110 and engaging tip 122 may be produced in any size for mating with various sizes of set screws. It is further contemplated that for the purpose of this disclosure, engaging tip 122 is not limited to the precise shape described and illustrated. The illustrated engaging tip 122 includes six ridges 132 and six elongate grooves 134, however, the engaging tip 122 may have any number of ridges and grooves surrounding circular base 130. For example, engaging tip 122 may have only two ridges protruding from circular base 130 positioned 180 degrees apart, resembling the shape of a flat-head screwdriver, or four ridges protruding from circular base 130 spaced 90 degrees apart resembling the shape of a phillips-head screwdriver. Further, the ridges may have a flat or sharp peak along the radially outermost surface, rather than the rounded peak as illustrated. The general purpose of engaging tip 122 is to form a first connection with the set screw such that the driver 100 can be rotatably fixed to the set screw, and may have any shape that will suitably form the desired connection while still defining a cavity 125 therethrough.

Figure 4:
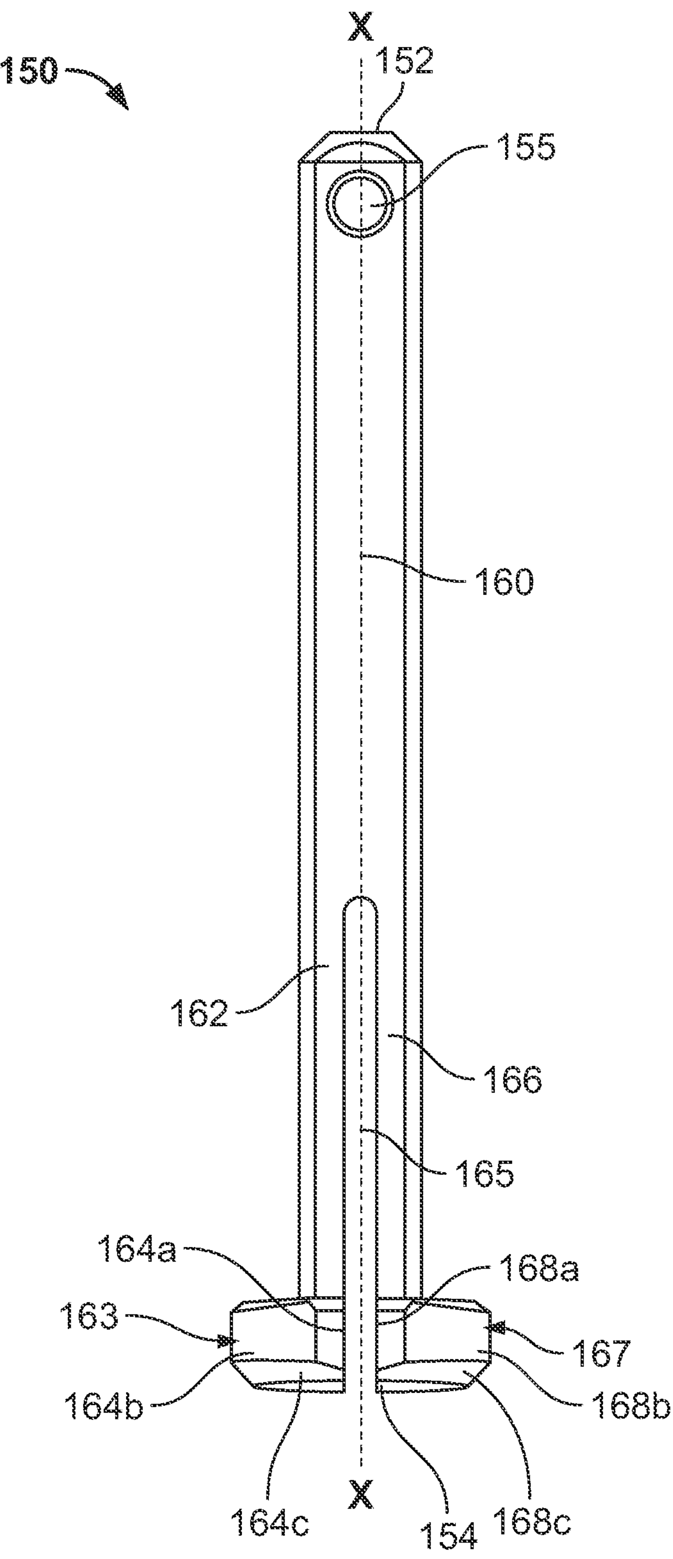
FIG. 4 is a front view of a compressible engagement member of the retaining driver of FIG. 1.

FIG. 4 illustrates a compressible engagement member 150 which is removably coupleable to drive shaft 110. Compressible engagement ember 150 is generally elongate, extending from a proximal end 152 to a distal end 154 along longitudinal axis X. Compressible engagement member 150 includes a stem 160 extending from proximal end 152, the stem 160 defining an aperture 155 proximate to proximal end 152. Extending distally from the stem 160 are a first branch 162 and a second branch 166. Branches 162, 166 are generally elongate, each extending parallel to axis X and defining a gap 165 therebetween. Branches 162, 166 may be sized such that the sum of the width (i.e., the distance in a direction orthogonal to longitudinal axis X) of the first branch 162, the gap 165, and the second branch 166 is equivalent to the width of the stem 160. A first head 163 is coupled to a distal end of the first branch 162, and a second head 167 is coupled to a distal end of the second branch 166. The first head 163 and the second head 167 are generally symmetrical about axis X in the view shown in FIG. 4 and are also separated by the gap 165, which is continuous and extends from the region between the branches 162, 166 to the region between the heads 163, 167. The first head 163 has a flat interior surface 164*a* adjacent to the gap 165 facing the second head 167, the interior surface 164*a* generally aligned with an inner edge of the first branch 162. The first head 163 further has a rounded outer surface 164*b* which flares radially outward beyond the first branch 162, and a tapering surface 164*c* between the rounded outer surface 164*b* and a distal end of the first head 163. The second head 167 has a flat interior surface 168*a* adjacent to the gap 165 facing the first head 163, the interior surface 168*a* generally aligned with an inner edge of the second branch 166. The second head 167 further has a rounded outer surface 168*b* which flares radially outward beyond the second branch 166, and a tapering surface 168*c* between the rounded outer surface 168*b* and a distal end of the second head 167.

It should be noted that compressible engagement member 150 is illustrated in FIG. 4 at rest, but may be configured to be compressed such that the first and/or second heads 163, 167 move with respect to each other, thereby changing the size of the gap 165 therebetween. For example, when the compressible engagement member 150 is inserted into the corresponding receiving portion of a set screw, the tapering surfaces 164*c*, 168*c* of the first and second head portions 163, 167, respectively, contact the set screw, which applies a compressive (i.e., radially inward) force to the first and second heads 163, 167 pushing the heads closer together until the inner surfaces 164*a*, 168*a* of each head contact each other. When the heads 163, 167 of the compressible engagement member 150 are pushed toward each other in the compressed configuration, the heads may be inserted into the receiving portion of a set screw, forming a stable connection between the compressible engagement member 150 and the set screw which may hold the set screw in engagement with the retaining driver 100 to be more easily handled and implanted. It is contemplated that the branches 162, 166 may be formed such that they are not be parallel to each other when the compressible engagement member 150 is at rest. In other words, the branches 162, 166 may extend radially inwardly from the stem 160 at rest to decrease the biasing force applied by the heads 163, 167, or the branches 162, 166 may extend radially outwardly from the stem 160 at rest to increase the biasing force applied by the heads 163, 167 when the retaining driver 100 is engaged with the fastener, as described below in greater detail.

Figure 5:
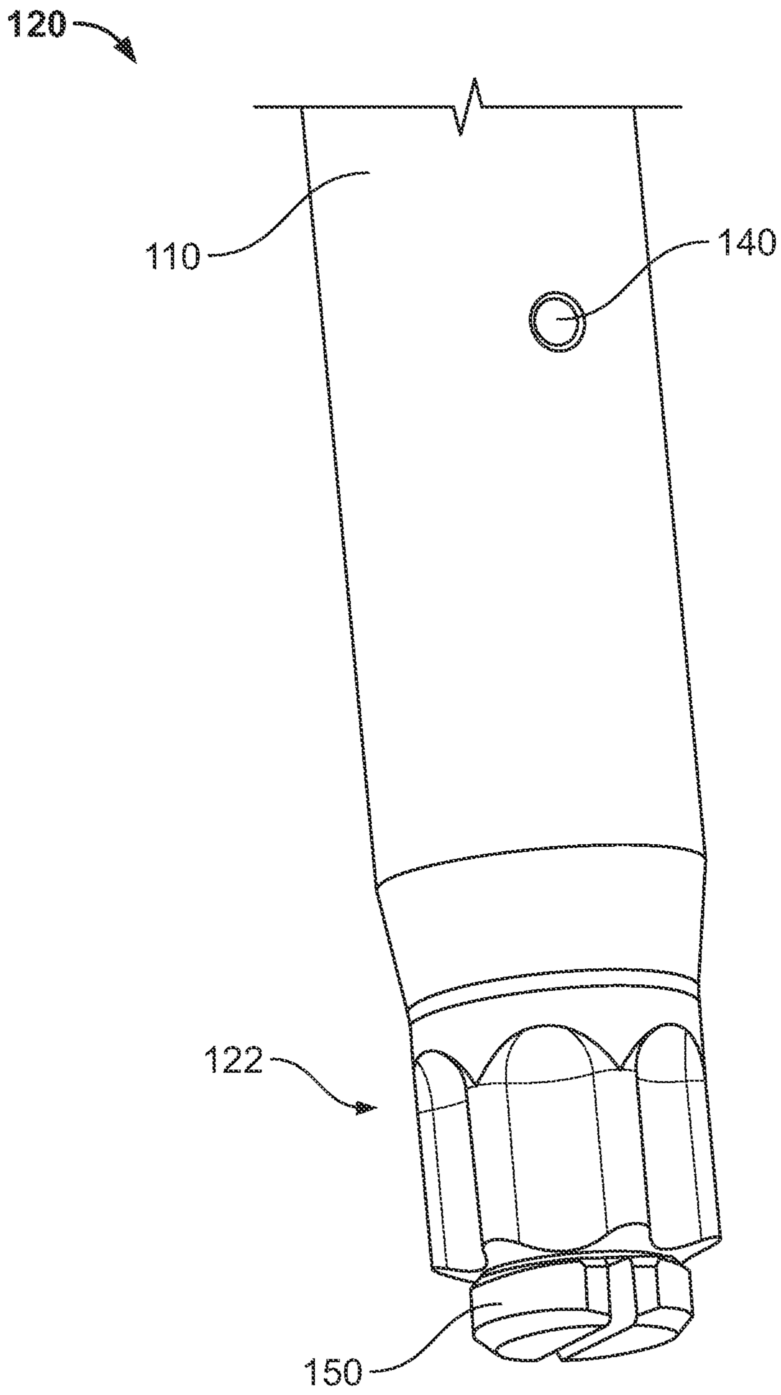
FIGS. 5-7 are close-up side, perspective and distal views, respectively, of the retaining driver of FIG. 1.
Figure 6:
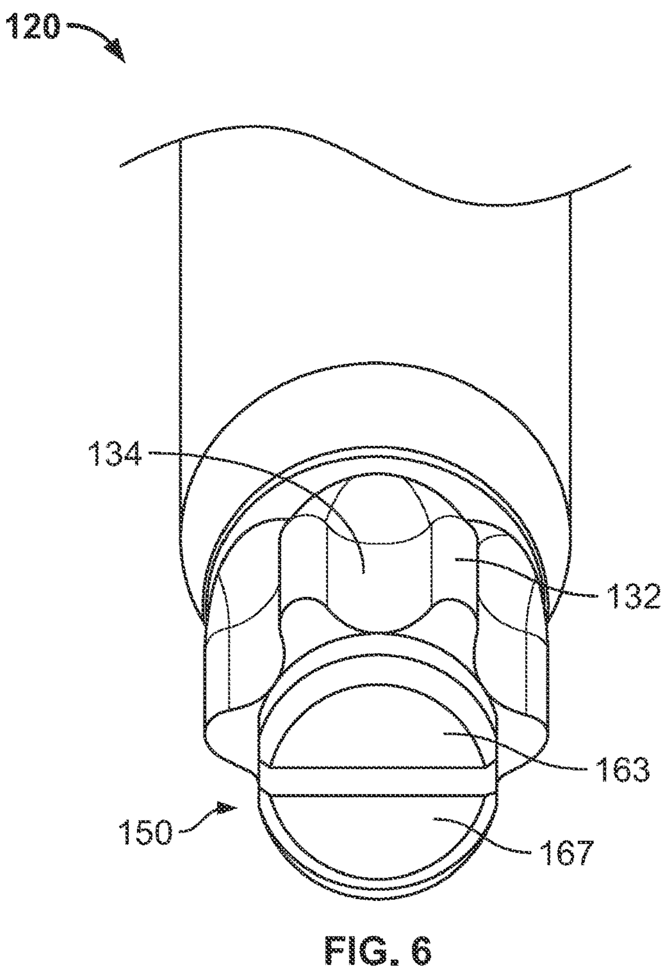
Figure 7:
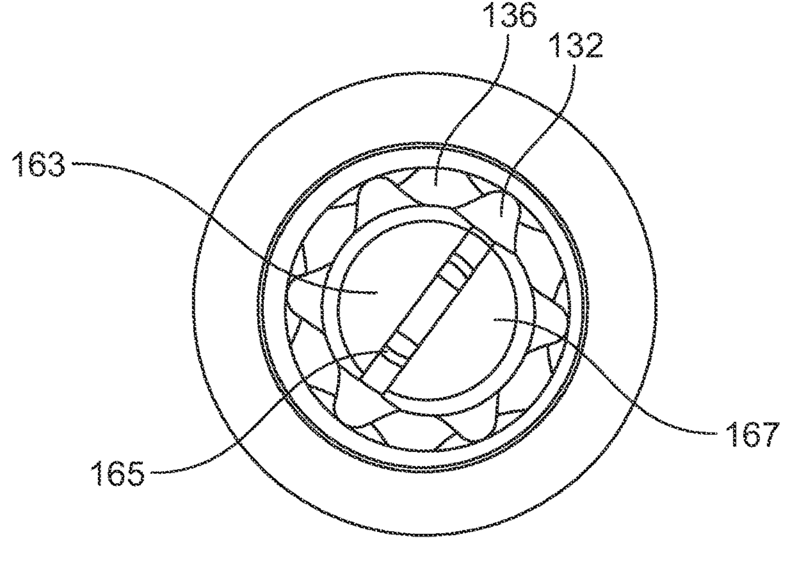

FIGS. 5-7 illustrate distal portion 120 of driver 100 with the compressible engagement member 150 coupled to the drive shaft 110. Compressible engagement member 150 is positioned within the cavity 125 of drive shaft 110 such that the stem 160 extends into distal portion 120 with at least a portion of the compressible engagement member 150 extending distally from engaging tip 122. Compressible engagement member 150 may be coupled to drive shaft 110 by aligning aperture 155 of compressible engagement member 150 with aperture 140 of drive shaft 110 and inserting a fixation device (such as a pin or a screw, preferably a cross-pin) through both apertures to couple the two structures together. Drive shaft 110 may include a second aperture aligned with and opposite aperture 140, such that the fixation device may be inserted through both apertures of the drive shaft 110 and pass through the aperture 155 of the compressible engagement member 150 to securely couple the compressible engagement member 150 to the drive shaft 110. It is contemplated that the fixation device may be removed to decouple the compressible engagement member 150 from the drive shaft 110, and a new compressible engagement member may be inserted into the drive shaft 110 and coupled thereto by the same or another fixation device. Such an ability to decouple and replace the compressible engagement member 150 may provide utility to the retaining driver 100 when used in any setting, particularly surgical settings. For instance, a used compressible engagement member 150 may be removed and replaced with a clean, new and/or sterilized compressible engagement member for continued use of the retaining driver 100 without the need to sanitize the driver. Further, removal of the compressible engagement member 150 may improve ease of sterilizing the surrounding parts of the retaining driver 100, such as the engaging tip 122 and the inner parts of the drive shaft 110 adjacent the cavity 125. Still further, the compressible engagement member 150 may be subject to fracturing, breakage, or undesired bending as a result of being frequently exposed to compression as described above, and therefore may often need replacing to ensure the retaining driver performs optimally in use.

When the retaining driver 100 is at rest (i.e., undeformed) in the assembled configuration as shown in FIGS. 6-7, the first head portion 163 and the second head portion 167 of the compressible engagement member 150 extend distally from engaging tip 122, the head portions 163, 167 separated by the gap 165. Head portions 163, 167 have rounded outer surfaces 164*b*, 168*b* and are sized and shaped such that their outer edges generally align with the circumference of circular base 130, and the ridges 132 extend radially outward beyond the edges of head portions 163, 167. The head portions 163, 167 are sized and shaped to collectively engage with the receiving portion of a set screw having a corresponding size and shape for receiving the head portions 163, 167. For example, at least part of the receiving portion of the set screw may be generally circular, and when the compressible engagement member 150 is in a resting configuration, the head portions 163, 167 may each have a generally semi-circular distal surface separated by the gap 165, causing the head portions 163, 167 to have a collective width greater than the corresponding receiving portion of the set screw. In the compressed configuration, however, (e.g., one or both of head portions 163, 167 is/are subject to a radially inward force as described above), the interior surfaces 164*a*, 168*a* of head portions 163, 167 may abut each other, and the semi-circular distal surfaces of the head portions 163, 167 may form a full circle having a radius substantially equal to, or slightly less than, that of the corresponding receiving portion of the set screw. Thus, when the head portions 163, 167 are engaged with the set screw in the compressed configuration, the head portions 163, 167 apply a biasing force in the radially outward direction onto the surrounding receiving portion of the set screw, thereby increasing friction and strengthening the engagement between the compressible engagement member 150 and the set screw. In other words, the set screw can be held in registration with the driver because of this relationship. It is contemplated that the head portions may have any shape suitable for being compressed to abut each other and fit within a corresponding shape of a receiving portion of a set screw. For example, each head portion may have a rectangular or triangular shape, with their interior surfaces being flat.

In a method of using the retaining driver 100, the driver 100 may be received by a surgeon in a fully assembled configuration, i.e., with the compressible engagement member 150 coupled to the drive shaft 110 by a fixation device inserted through the aperture 140 of the drive shaft and the aperture 155 of the compressible engagement member 150. The surgeon may then use the tool by engaging a corresponding receiving portion of a set screw with the head portions 163, 167 of the compressible engagement member 150 and further engaging a corresponding receiving portion of the set screw with the engaging tip 122. When implanting a spinal rod into a patient, the spinal rod may be inserted into a plurality of coupling elements of pedicle screws anchored into the pedicles of the spine. The surgeon may thereafter use the driver 100 by pointing the distal end 104 into the coupling element to actuate a set screw over the spinal rod, thereby securing the spinal rod with the coupling element to create a stable fixation of the spinal rod to the spinal cord. The retaining driver 100 may then be completely disengaged from the set screw. If desired, the compressible engagement member 150 may be decoupled from the drive shaft 110 by removing the fixation device inserted through the apertures to couple the compressible engagement member 150 to the drive shaft 110. A replacement compressible engagement member may then be coupled to the drive shaft 110 by inserting the proximal end of the replacement compressible engagement member into the cavity 125 at the distal end 104 of the drive shaft 110 to align the aperture 155 of the compressible engagement member 150 with the aperture of the drive shaft 110. The same or another fixation device may then be inserted through the apertures of the drive shaft and the new compressible engagement member to couple the two pieces together, and the retaining driver 100 may then be used in the manner as described above. It is also contemplated that the retaining driver 100 may be delivered to a surgeon in a kit, which may include the drive shaft 110 having engaging tip 122, one or a plurality of compressible engagement members 150, and one or a plurality of fixation devices for coupling a compressible engagement member to the drive shaft.

Figure 8:
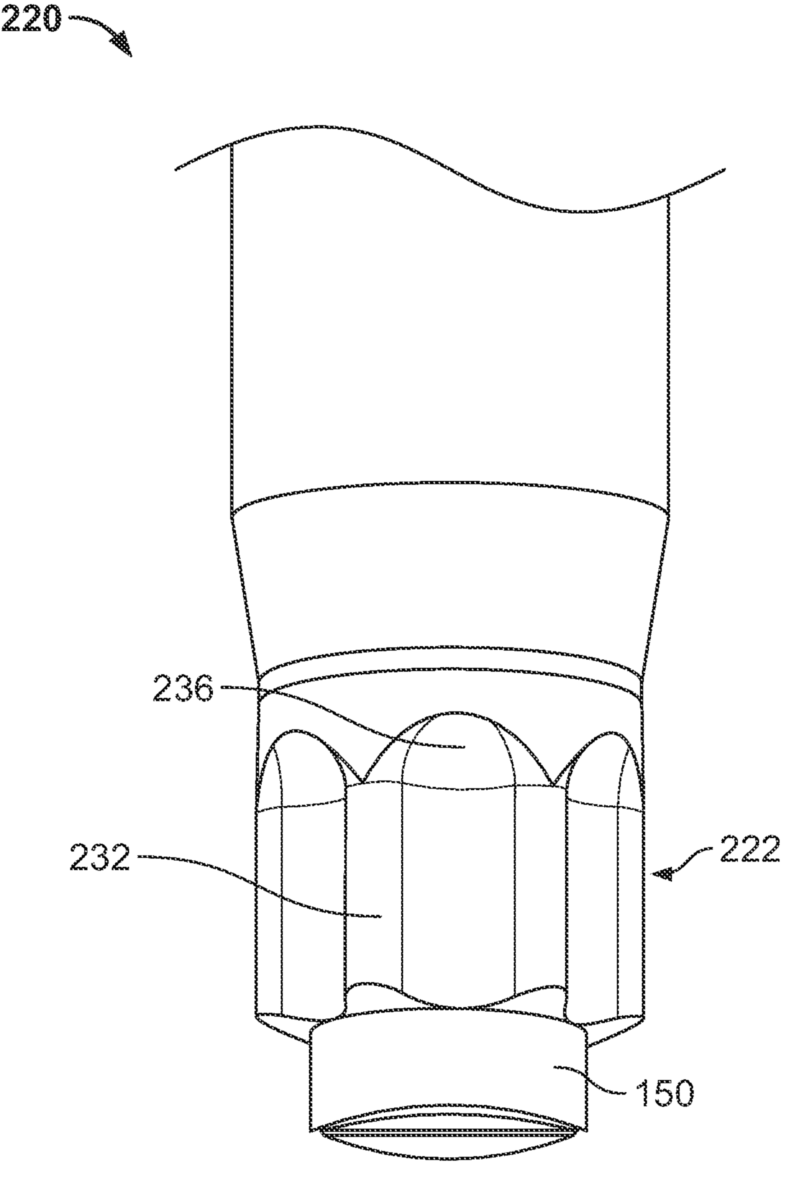
FIG. 8 is a front view of a distal portion of a retaining driver according to another embodiment of the disclosure.

FIG. 8 illustrates a distal portion 220 of a retaining driver according to another embodiment of the disclosure. Unless otherwise stated, like reference numerals refer to like elements of the above-described retaining driver 100, but within the 200-series of numbers. Engaging tip 222 is substantially similar to engaging tip 122 with the exception that engaging tip 222 lacks elongate grooves between ridges 232. That is, ridges 232 are finger-like extensions defining gaps between each adjacent pair of ridges 232. Engaging tip 222 includes proximal rounded grooves 236 similar to engaging tip 122, but lacks grooves located immediately distal to the proximal rounded grooves 236. Such a structure may form a unique connection with the receiving portion of a set screw. It is contemplated that an engaging tip of a retaining driver may have a combination of engaging tip 122 and engaging tip 222, such as half of the engaging tip having the structure of engaging tip 122 with grooves 134, and the other half of the engaging tip having the structure of engaging tip 222 without any grooves.

Figures 9, 10:
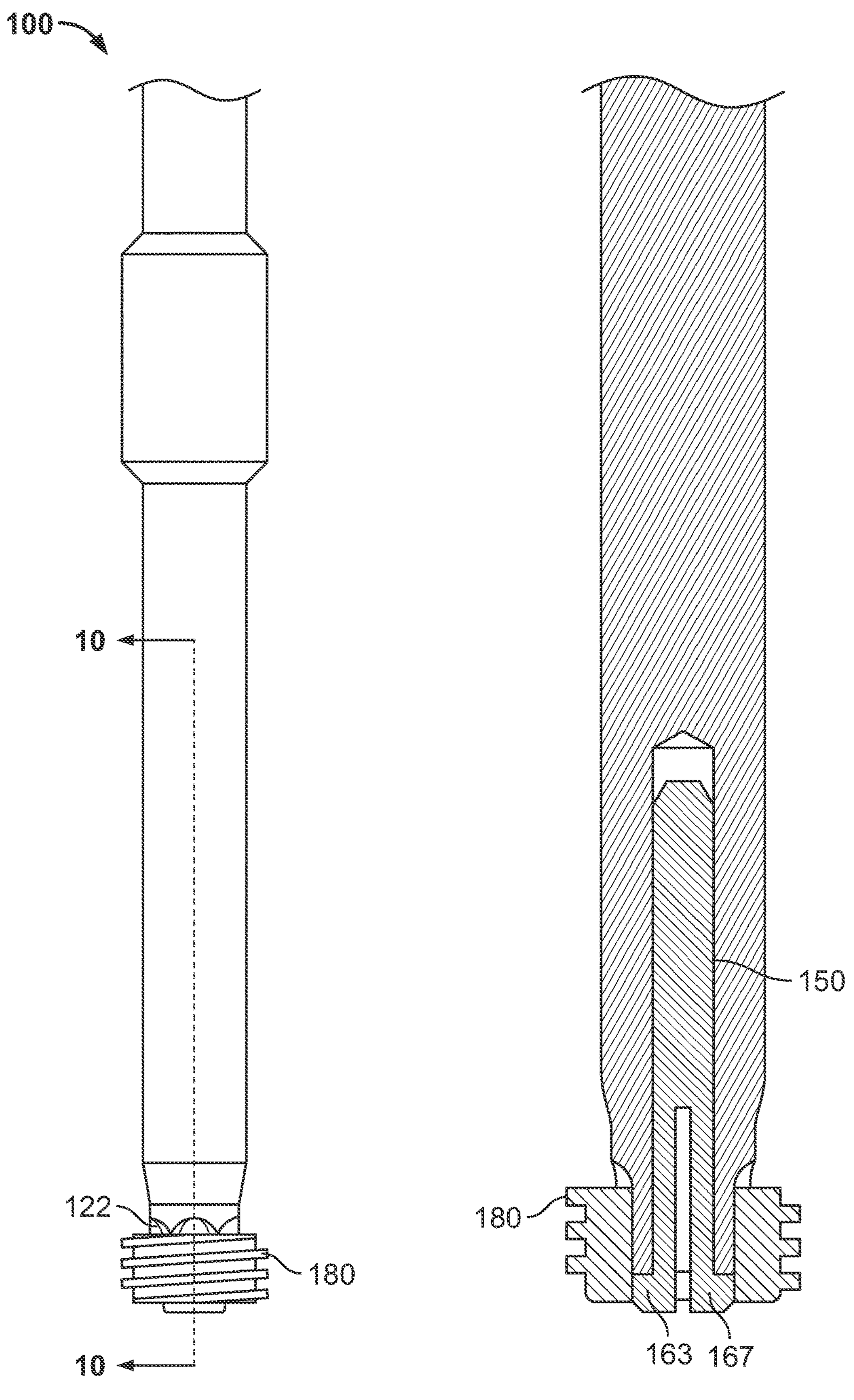
FIG. 9 is a front view of the retaining driver of FIG. 1 engaged with a set screw.
FIG. 10 is a cross-sectional view along line A-A of the retaining driver of FIG. 9.

FIGS. 9-10 illustrate the retaining driver 100 engaged with a set screw 180. As described above, set screw 180 includes a receiving portion sized and shape to receive and mate with the engaging tip 122 of the retaining driver 100 as shown in FIG. 9. The engagement between the engaging tip 122 and the set screw 180 rotationally fixes the driver 100 to the set screw 180 such that rotation of the driver 100 causes rotation of the set screw 180. As shown in the cross-sectional view of FIG. 10, the compressible engagement member 150 having head portions 163, 167 extending distally beyond the engaging tip 122 is inserted into a receiving portion of the set screw 180 and inwardly compressed by the set screw 180. The compressible engagement member 150 may be formed of a material having a stiffness that causes a radially outward biasing force from the member 150 to return to its resting state. As such, the head portions 163, 167 abut the receiving portion (e.g., the interior walls of the screwhead) of the set screw 180 and increase the frictional force between the head portions 163, 167 and the set screw 180 to increase the force required to disengage driver 100 from the set screw 180.

As noted above, any embodiments of the retaining driver described herein be used in any context requiring a strong detachable engagement between the tool and another object, particularly a fastening device that requires rotation. For example, the retaining driver may be used in carpentry, construction, mechanical repairs, etc. with fasteners such as wood screws, metal screws, pins, bolts, nails etc. shaped to mate with the engaging tip and compressible engagement member of the retaining driver. The tool may also be used for the removal of the same or similar objects, particularly in too-far-to-reach locations, such as the ceiling of a room. For instance, engaging the tool with a fastener implanted in the ceiling may allow easy rotation of the fastener from the ground level and a steady grip with the fastener after it has been removed from its respective site to hold the fastener at the distal end of the tool and safely bring it down without the risk of it falling on the user.

Any shape is contemplated for the engaging tip. In some examples, instead of being formed with the ridges 132 of retaining driver 100, the engaging tip 122 may be formed with an external threading size and shaped to engage a female threaded receiving portion of a fastener. In such examples, the retaining driver may be used to engage a fastener by inserting the head portions of the compressible engagement member in a corresponding receiving portion of the fastener and rotating the retaining driver relative to the fastener to mate the threaded engaging tip with the corresponding threaded receiving portion of the fastener. The initial rotation may secure the retaining driver to the fastener, and further rotation may cause rotation of the fastener to implant the fastener as desired.

In certain preferred embodiments, the components of the retaining driver may be formed of stainless steel. It is contemplated that any or all of the components of the retaining driver may be made of metals such as, titanium, carbon steel, aluminum, or the like, or other spring materials used particularly for the compressible engagement member such as nitinol. It is further contemplated that any or all of the components of the retaining driver may be formed of polymeric materials such as plastics, polyethylene terephthalate (PET), polyether ether ketone (PEEK), or the like. Certain components may be formed from different materials than other components. For example, the drive shaft and/or the engaging tip may be formed from a different material than the compressible engagement member. Any suitable length is contemplated for the retaining driver. In certain preferred embodiments, the compressible engagement member may measure between approximately 4 mm and 5 mm in diameter, preferably 4.5 mm, when in the compressed configuration to fit with the corresponding receiving portion of a screw. In other embodiments the compressible engagement member may measure about 1 mm in diameter in the compressed configuration, e.g., for craniomaxillofacial applications. In still further embodiments, the compressible engagement member may measure between about 10 mm and about 12 mm in diameter in the compressed configuration for larger applications, such as hip surgery.

Figures 11, 12:
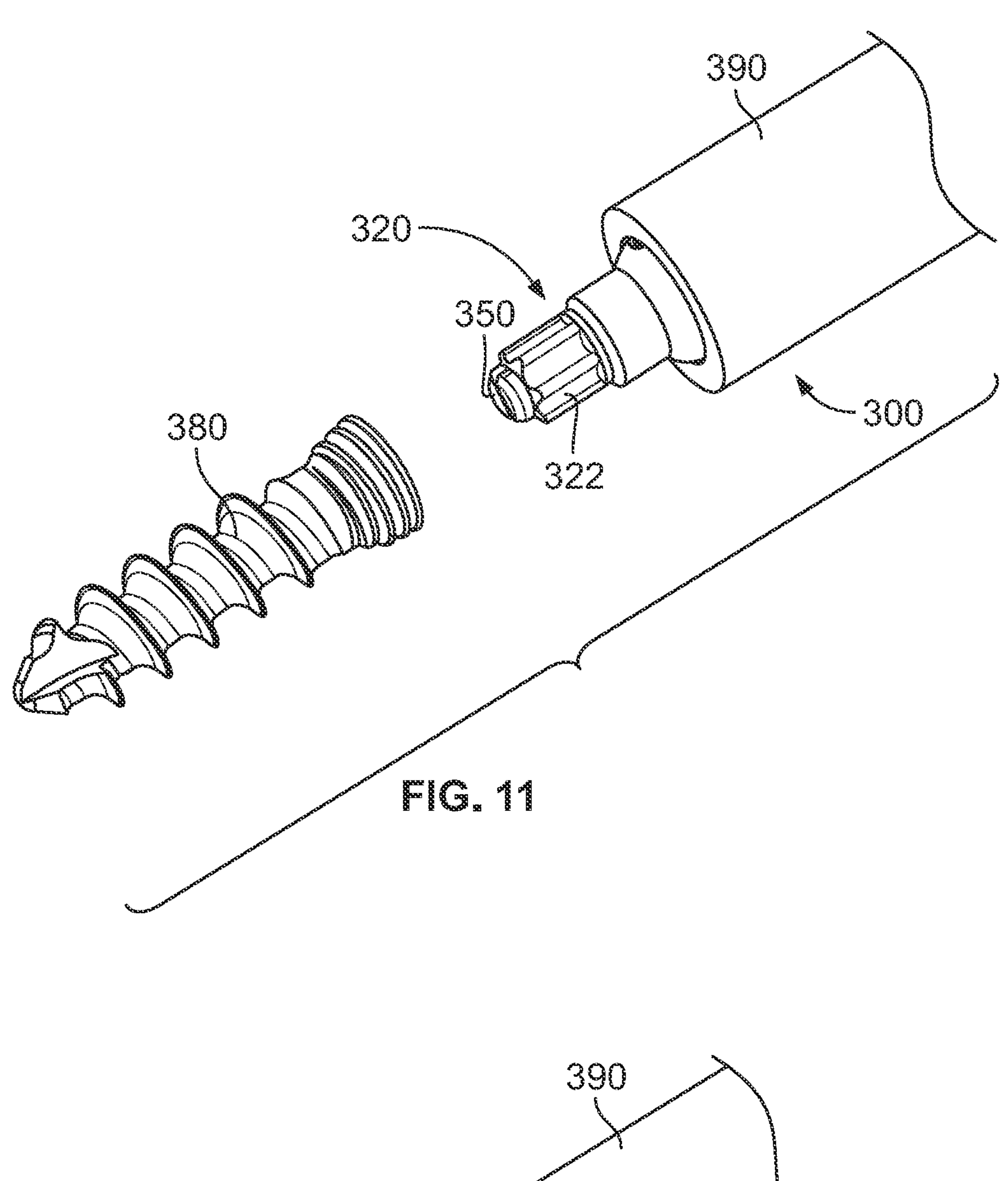
FIGS. 11-12 are side views of a retaining driver engagement with a screw according to another embodiment of the disclosure.
Figure 13:
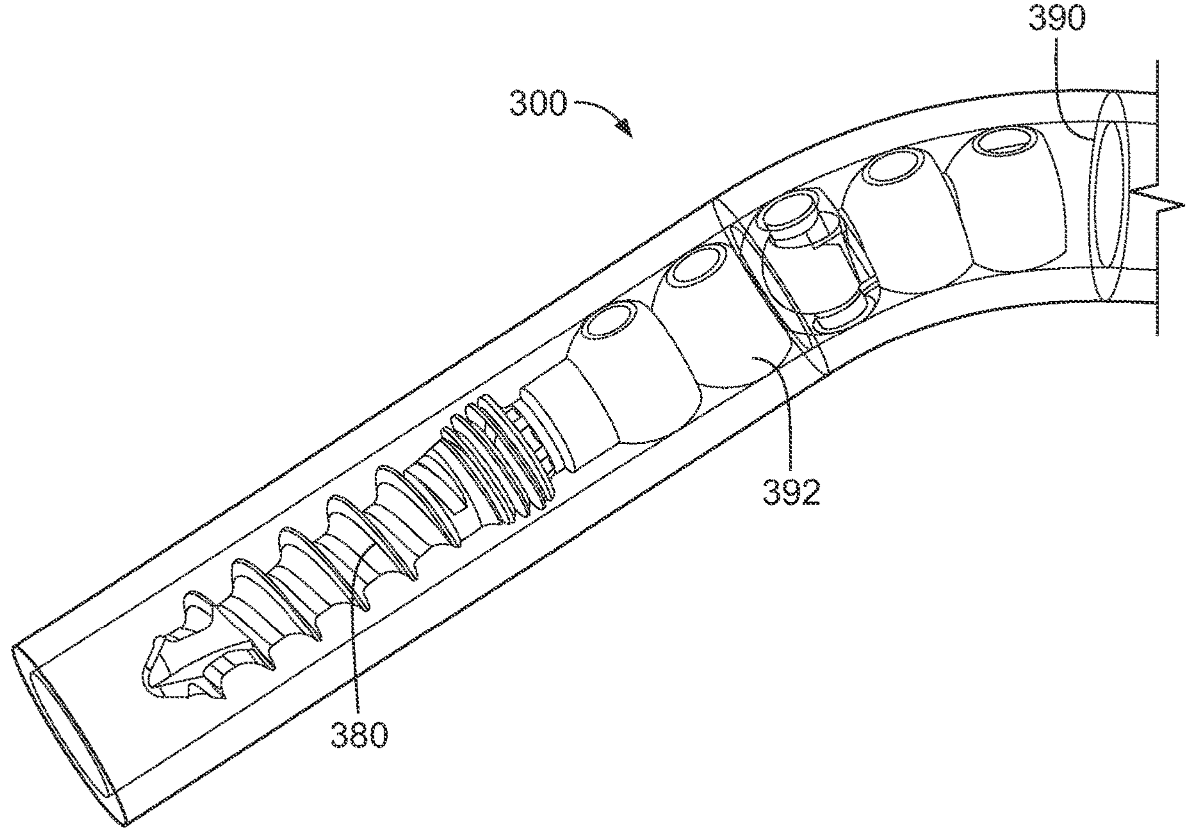
FIG. 13 is a transparent side view of the retaining driver of FIG. 12.

FIGS. 11-13 illustrate a retaining driver 300 according to another embodiment of the disclosure. Unless otherwise stated, like reference numerals refer to like elements of the above-described retaining driver 100, but within the 300-series of numbers. Retaining driver 300 includes a distal portion 320 substantially similar to distal portion 120, having engaging tip 322 and compressible engagement member 350. In the present embodiment, distal portion 320 is disposed within a rigid guide 390. Retaining driver 300 may be wielded by an operator such that distal portion 320 may be one of or both translated and rotated relative to the guide 390. FIGS. 11 and 12 illustrate the engagement of the retaining driver 300 with a screw 380, which may occur in the manner described above with respect to retaining driver 100 and set screw 180. FIG. 13 shows the guide 390 having a curved shape and a plurality of rounded linkages 392 connected in series which allow for the rotation and translation of distal portion 320 relative to guide 390. The relationship between each of the rounded linkages 392 and the guide 390 are described in greater detail in U.S. Provisional Patent Application 63/180,234, the disclosure of which is hereby incorporated by reference herein. As shown in FIG. 13, the distal portion 320 may be translated proximally relative to the guide 390 such that the distal portion 320 and the screw 380 are disposed within the guide 390. With the screw 380 positioned within the guide 390, the retaining driver 300 may be manipulated by the operator to be positioned into hard-to-reach locations without the risk of the screw 380 contacting an external object and causing disengagement of the screw 380 from the retaining driver 300. Placing the screw 380 within the guide 390 may also prevent the screw 380 from causing damage to surrounding objects, for instance, when using the driver 300 in surgery and transporting the screw around delicate tissue. Forming a strong engagement between the distal portion 320 and the screw 380 is a critical feature in the present embodiment to allow the screw 380 to be translated and rotated in conjunction with the distal portion 320 without decoupling prior to placement or implantation of the screw 380.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims

The invention claimed is:

1. A tool for use with a fastener, the tool comprising:

a drive shaft extending along a longitudinal axis from a proximal end to a distal end, the drive shaft including a cavity;

an engaging tip at the distal end, the engaging tip sized and shaped to detachably engage a fastener, wherein the engaging tip is rotationally fixed to the fastener when the engaging tip is engaged with the fastener;

a compressible engagement member detachably coupled to the drive shaft, the compressible engagement member extending from the engaging tip sized and shaped to detachably engage with a receiving portion of the fastener, the compressible engagement member including a stem extending into the cavity, the stem defining an aperture therethrough for receiving a fixation device, wherein in an undeformed configuration, the compressible engagement member has a width greater than the receiving portion.

2. The tool of claim 1, wherein in a compressed configuration, the compressible engagement member has a width less than the receiving portion.

3. The tool of claim 1, wherein the drive shaft has a distal portion adjacent the engaging tip, and wherein the engaging tip and the distal portion define the cavity extending along the longitudinal axis.

4. The tool of claim 3, wherein the compressible engagement member extends along the longitudinal axis from a proximal end to a distal end.

5. The tool of claim 4, wherein the compressible engagement member includes a first branch and a second branch extending distally from the stem.

6. The tool of claim 5, wherein the compressible engagement member includes a first head portion coupled to a distal end of the first branch and a second head portion coupled to a distal end of the second branch.

7. The tool of claim 6, wherein when the compressible engagement member is in the undeformed configuration, the first and second branches define a first gap therebetween and the first and second head portions define a second gap therebetween in communication with the first gap.

8. The tool of claim 7, wherein the first and second head portions have a tapered distal surface sized and positioned to contact the fastener when the tool is being engaged with the fastener, such that the fastener applies a compressive force to the head portions to transition the compressible engagement member from the undeformed configuration to a compressed configuration.

9. The tool of claim 1, wherein the drive shaft defines a first aperture configured to receive the fixation device.

* * * * *